United States Patent [19]
Robinson

[11] Patent Number: 6,071,501
[45] Date of Patent: Jun. 6, 2000

[54] PHOTOSTABLE UV PROTECTION COMPOSITIONS

[75] Inventor: Larry Richard Robinson, Loveland, Ohio

[73] Assignee: The Procter & Gamble Company, Cincinnati, Ohio

[21] Appl. No.: 09/244,727

[22] Filed: Feb. 5, 1999

[51] Int. Cl.[7] .............................. A61K 7/42; A61K 7/00
[52] U.S. Cl. ............................ 424/59; 424/60; 424/400; 424/401
[58] Field of Search ................. 424/59, 60, 400, 424/401

[56] References Cited

U.S. PATENT DOCUMENTS

| | | | |
|---|---|---|---|
| 4,387,089 | 6/1983 | De Polo | 424/59 |
| 4,489,057 | 12/1984 | Welters et al. | 424/47 |
| 5,152,983 | 10/1992 | Nambudiry et al. | 424/60 |
| 5,538,716 | 7/1996 | Forestier et al. | 424/59 |
| 5,549,886 | 8/1996 | Grollier | 424/59 |
| 5,567,418 | 10/1996 | Forestier et al. | 424/59 |
| 5,576,354 | 11/1996 | Deflandre et al. | 514/685 |
| 5,587,150 | 12/1996 | Deflandre et al. | 424/59 |
| 5,605,680 | 2/1997 | Deflandre et al. | 424/59 |
| 5,618,520 | 4/1997 | Hansenne et al. | 424/59 |
| 5,620,682 | 4/1997 | Fogel | 424/60 |
| 5,624,663 | 4/1997 | Deflandre et al. | 424/59 |
| 5,667,765 | 9/1997 | Hansenne et al. | 424/59 |
| 5,672,337 | 9/1997 | Ascione et al. | 424/59 |
| 5,783,174 | 7/1998 | Deckner et al. | 424/59 |

FOREIGN PATENT DOCUMENTS

| | | |
|---|---|---|
| 0 709 080 A1 | 5/1996 | European Pat. Off. . |
| 0 717 982 A1 | 6/1996 | European Pat. Off. . |
| 0 754 445 A2 | 1/1997 | European Pat. Off. . |
| 0 780 119 A1 | 6/1997 | European Pat. Off. . |
| 0 787 483 A1 | 8/1997 | European Pat. Off. . |
| 0 868 905 A2 | 10/1998 | European Pat. Off. . |
| 2 198 944 | 6/1988 | United Kingdom . |
| WO 97/21422 | 6/1997 | WIPO . |

*Primary Examiner*—Shelley A. Dodson
*Attorney, Agent, or Firm*—Dara M. Kendall; Loretta J. Henderson; Michael E. Hilton

[57] ABSTRACT

The present invention relates to photostable compositions suitable for providing protection against the harmful effects of ultraviolet radiation. The compositions provide excellent efficiency and broad spectrum UV efficacy while exhibiting improved photostability. Methods of use for these compositions are also disclosed. The present compositions comprise:

a) an effective amount of a UVA-absorbing dibenzoylmethane sunscreen active;

b) a photostabilizing system consisting essentially of an effective amount of 2-ethylhexyl-p-methoxycinnamate; and c) a suitable carrier;

wherein the mole ratio of 2-ethylhexyl-p-methoxycinnamate to the dibenzoylmethane sunscreen active is from about 0.15:1 to about 1:1.

21 Claims, No Drawings

PHOTOSTABLE UV PROTECTION COMPOSITIONS

TECHNICAL FIELD

The present invention relates to photostable compositions suitable for providing protection against the harmful effects of ultraviolet radiation wherein the compositions have excellent efficiency and broad spectrum UV efficacy. The compositions which exhibit improved and unexpected photostability comprise a UVA-absorbing dibenzoylmethane sunscreen active, a photostabilizing system containing 2-ethylhexyl-p-methoxycinnamate and a suitable carrier such that the mole ratio of 2-ethylhexyl-p-methoxycinnamate to UVA-absorbing dibenzoylmethane sunscreen active is from about 0.15:1 to about 1:1.

BACKGROUND OF THE INVENTION

It is well known that exposure to sunlight can pose a number of hazards to the skin. These damaging effects may result not only from sunbathing but also from the sunlight exposure associated with daily outdoor activities. The major short term hazard of prolonged exposure to sunlight is erythema, i.e., sunburn, which primarily results from UVB radiation having a wavelength of from about 290 nm to about 320 nm. Over the long term, however, malignant changes in the skin surface often occur. Numerous epidemiologic studies demonstrate a strong relationship between sunlight exposure and human skin cancer. Another long term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. The adverse effects associated with exposure to UV radiation are more fully discussed in DeSimone, "Sunscreen and Suntan Products," *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation," *International Journal of Cosmetic Science*, 4, pp. 15–24 (1982).

As a result of the abovementioned hazards associated with sunlight exposure, the general public's interest in the sun protection product market has grown considerably. Today, there are not only sunscreen products for sunbathing but there are also a variety of personal care products containing sunscreens, particularly cosmetic type products which are worn daily. "Personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage.

Many conventional sunscreen products, in particular, are deficient, however, due to their inability to provide efficacious protection against broad spectrum UV radiation, i.e., protection against both UVB and UVA radiation. Today, most commercially available sunscreen products are efficient at absorbing UV radiation in the 290 nm to 320 nm UVB region such that sunburn of the skin is prevented. They are less efficient when it comes to absorbing light which falls in the 320 nm to 400 nm UVA region, which leaves the skin vulnerable to premature skin aging. This deficiency is due in part to the limited number of UVA absorbing sunscreen actives which are both commercially available and approved for global use. One class of these sunscreen actives includes dibenzoylmethane compounds which provide broad spectrum UV protection and are described in U.S. Pat. No. 4,387,089, issued to De Polo on Jun. 7, 1983 and U.S. Pat. No. 4,489,057, issued to Welters et al. on Dec. 18, 1984. 4-tert-butyl-4'-methoxydibenzoylmethane, in particular, is approved for global use. Unfortunately, when used individually in sunscreen products, most dibenzoylmethane compounds tend to photodegrade upon exposure to UV radiation thereby reducing their UVA efficacy. Furthermore, it is well known that even when dibenzoylmethane compounds are used in combination with other sunscreen actives, severe photodegradation still tends to occur. For instance, U.S. Pat. No. 4,387,089 proposes to combine 4-(1,1 dimethylethyl)-4'-methoxydibenzoylmethane with various UVB sunscreen actives, namely 2-ethylhexyl-p-methoxycinnamate (also referred to as octyl methoxycinnamate), for the purpose of absorbing all of the UV radiation between 280 and 380 nm and in which case it is stated that the ratio of the dibenzoylmethane sunscreen active to the UVB sunscreen active is not critical. In fact, it is well known that the combination of about 1-3% 4-tert-butyl-4'-methoxydibenzoylmethane and 6–7.5% 2-ethylhexyl-p-methoxycinnamate results in a formulation in which both of the sunscreen actives are photounstable which in turn makes the overall formulation photounstable. Without being limited by theory, it is believed that upon exposure to UV radiation, 4-tert-butyl-4'-methoxydibenzoylmethane and 2-ethylhexyl-p-methoxycinnamate react with each other to form non-UV absorbing compounds.

Therefore, sunscreen products which include dibenzoylmethane sunscreen actives are typically more difficult to formulate due to their inherent lack of photostability. One approach to stabilize these types of sunscreens is described in U.S. Pat. No. 5,783,174 issued to Deckner on Jul. 21, 1998, which involves the use of benzylidene camphor sunscreens to stabilize the dibenzoylmethane compound. Such compositions, however, are not currently approved for global use on humans.

Thus, there is a need for photostable compositions suitable for providing protection against the harmful effects of UV radiation to human skin. In particular, in the personal care industry, a need remains for sunscreen products having excellent photostability, efficiency, and which provide broad spectrum UV protection (i.e., against both UVA and UVB radiation) in a safe and economical manner.

Likewise, in other industries such as the automotive care, marine vehicle care, household care, animal care, and coatings industries, UV radiation causes undesirable wear and damage. Therefore, a need exists for photostable compositions suitable for providing protection against the harmful effects of UV radiation to a variety of objects and/or materials prone to sun exposure.

In contrast to the common knowledge of those having ordinary skill in the art, Applicant has surprisingly found that the compositions of the present invention, which comprise a UVA-absorbing dibenzoylmethane sunscreen active, a photostabilizing system which includes 2-ethylhexyl-p-methoxycinnamate, and a suitable carrier such that the mole ratio of 2-ethylhexyl-p-methoxycinnamate to UVA-absorbing dibenzoylmethane sunscreen active is from about 0.15:1 to about 1:1, provide excellent photostability, efficiency, and UV protection efficacy (including both UVA and UVB protection), in a safe and economical manner.

SUMMARY OF THE INVENTION

The present invention relates to a photostable composition suitable for providing protection against the harmful effects of ultraviolet radiation comprising:

a) an effective amount of a UVA-absorbing dibenzoylmethane sunscreen active;

b) a photostabilizing system consisting essentially of an effective amount of 2-ethylhexyl-p-methoxycinnamate; and c) a suitable carrier;

wherein the mole ratio of 2-ethylhexyl-p-methoxycinnamate to the dibenzoylmethane sunscreen active is from about 0.15:1 to about 1:1.

In preferred embodiments, the UVA-absorbing dibenzoylmethane sunscreen active and 2-ethylhexyl-p-methoxycinnamate are present in "safe and effective" amounts and the mole ratio of 2-ethylhexyl-p-methoxycinnamate to UVA-absorbing dibenzoylmethane sunscreen active is preferably from about 0.3:1 to about 0.9:1, more preferably from about 0.45:1 to about 0.8:1, even still more preferably from about 0.6:1 to about 0.75:1, and most preferably from about 0.65:1 to about 0.75:1. The present invention also relates to methods for providing protection to skin from the harmful effects of UV radiation by topical application of such compositions. Furthermore, the present invention relates to methods of stabilizing a composition which comprises a UVA-absorbing dibenzoylmethane sunscreen active and 2-ethylhexyl-p-methoxycinnamate.

DETAILED DESCRIPTION OF THE INVENTION

The compositions of the present invention are useful for providing photostable protection against the harmful effects of ultraviolet radiation, especially to human skin. The essential components of these compositions are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molar weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including patents, patent applications, and printed publications, are hereby incorporated by reference in their entirety in this disclosure.

UVA-Absorbing Dibenzoylmethane Sunscreen Active

The compositions of the present invention comprise a UVA-absorbing dibenzoylmethane sunscreen active which absorbs UV radiation having a wavelength of from about 320 nm to about 400 nm. Preferred UVA-absorbing dibenzoylmethane sunscreen actives have the general structure

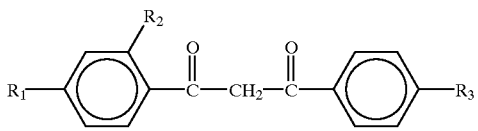

wherein $R_1$ substituent selected from the group consisting of H, OR, and NRR wherein each R is independently H, or $C_1$–$C_{20}$ straight or branched alkyls, $R_2$ is selected from the group consisting of H or OH, and $R_3$ is selected from the group consisting of H, or $C_1$–$C_{20}$ straight or branched alkyls. Even though the dibenzoylmethane chromophore is represented as a 1,3-diketone, it should be understood that this representation in no way excludes other tautomeric forms of the functional group such as the enol form. Thus, whenever the 1,3-diketone form is designated, it is understood that all appropriate enol tautomers are also contemplated and included herein. These tautomeric enol forms of the dibenzoylmethane chromophore can be represented by the following tautomeric structures.

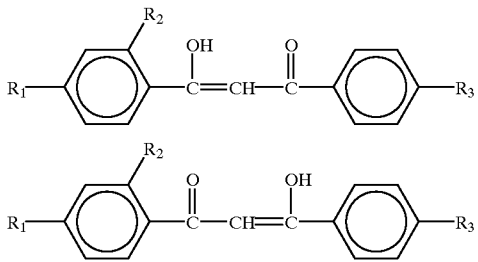

wherein $R_1$, $R_2$, and $R_3$ are defined as above. Examples of such UVA-absorbing dibenzoylmethane sunscreen actives are described in U.S. Pat. No. 4,489,057, issued to Welters et al. on Dec. 18, 1984 and U.S. Pat. No. 4,387,089, issued to Depolo on Jun. 7, 1983; and in *Sunscreens: Development, Evaluation, and Regulatory Aspects*, edited by N. J. Lowe and N. A. Shaath, Marcel Dekker, Inc. (1990).

Suitable UVA-absorbing dibenzoylmethane sunscreen actives include, but are not limited to, those selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof. Preferred UVA-absorbing dibenzoylmethane sunscreen actives include those selected from the group consisting of 4-tert-butyl-4'-methoxydibenzoylmethane, 4-isopropyldibenzoylmethane, and mixtures thereof. A more preferred UVA-absorbing dibenzoylmethane sunscreen active is 4-tert-butyl-4'-methoxydibenzoylmethane.

The sunscreen active, 4-tert-butyl-4'-methoxydibenzoylmethane, which is also known as butyl methoxydibenzoylmethane or Avobenzone, is commercially available under the names Parsol® 1789 from Givaudan-Roure (International) S.A. (Basel, Switzerland) and Eusolex® 9020 from Merck & Co., Inc. (Whitehouse Station, N.J.). The sunscreen 4-isopropyldibenzoylmethane, which is also known as isopropyl dibenzoylmethane, is commercially available from Merck under the name Eusolex 8020.

The UVA-absorbing dibenzoylmethane sunscreen active of the instant invention is present in an effective amount to provide broad spectrum UV protection either independently or in combination with other UV protective actives which may be present in the composition. As used herein, an "effective amount" means an amount of a compound, component, or composition (as applicable) sufficient to significantly induce a positive effect (e.g., photoprotection or improvement in photostability). Preferably, the UVA absorbing dibenzoylmethane sunscreen active is present in a "safe and effective amount" which, as used herein, means an amount of a compound, component, or composition (as applicable) sufficient to significantly induce a positive effect (e.g., photoprotection or improvement in photostability), but low enough to avoid serious side effects, (e.g., undue toxicity or allergic reaction), i.e., to provide a reasonable benefit to risk ratio, within the scope of sound medical judgment. The composition preferably contains from about 0.01% to about 30%, more preferably from about 0.1% to about 6%, and even more preferably from about 1% to about 3%, and most preferably from about 1.5% to about 2.5%, by weight of the composition, of the UVA-absorbing dibenzoylmethane sunscreen active. Exact amounts of the sunscreen active will vary depending upon the desired Sun Protection Factor, i.e., the "SPF" of the composition as well as the desired level of UVA protection. (SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register*, 43, No. 166, pp. 38206–38269, Aug. 25, 1978).

Photostabilizing System

The compositions of the present invention also comprise a photostabilizing system which consists essentially of 2-ethylhexyl-p-methoxycinnamate. The photostabilizing system is useful for reducing the photodegradation, i.e., the photoinstability, of the UVA-absorbing dibenzoylmethane sunscreen active as well as the photodegration of the composition of the present invention. Photodegradation may be determined by a reduction of the UV absorption capability which in turn may be measured by using standard UV absorbance methods. Preferred compositions retain at least about 75%, more preferably at least about 85%, and most preferably at least about 95%, of their initial UV absorption after irradiation with approximately 2 J/cm$^2$ per desired SPF unit of broad band UV radiation, e.g., 30 J/cm$^2$ for an SPF 15 composition. The 2-ethylhexyl-p-methoxycinnamate is present in the photostabilizing system in an amount such that the mole ratio of 2-ethylhexyl-p-methoxycinnamate to UVA-absorbing dibenzoylmethane sunscreen active is from about 0.15:1 to about 1:1, preferably from about 0.3:1 to about 0.9:1, more preferably from about 0.45:1 to about 0.8:1, even more preferably from about 0.6:1 to about 0.75:1, and most preferably from about 0.65:1 to about 0.75:1.

Carrier

The compositions of the present invention comprise a suitable carrier or vehicle for the UVA-absorbing dibenzoylmethane sunscreen active, the photostabilizing system, and any optional components. Suitable carriers are well known in the art and are selected based on the end use application. For example, carriers of the present invention include, but are not limited to, those suitable for application to skin, hair, nails, animal skin, fur, automobiles, fabrics, marine vehicles, as well as those suitable for incorporation into plastics, metals, etc. Preferably, the carriers of the present invention are suitable for application to skin (e.g., sunscreens, creams, milks, lotions, masks, serums, etc.); hair and fur (e.g., shampoos, hair setting or treatment gels or lotions, shaping/curling/fixation lacquers or lotions, etc.); and nails (e.g., polishes, treatments, etc.). In preferred embodiments, the carrier is suitable for application to skin which means that the carrier and its components are suitable for use in contact with skin, hair, fur, and nails without undue toxicity, incompatibility, instability, allergic response, and the like within the scope of sound medical judgment. Such carriers are well-known to one of ordinary skill in the art, and can include one or more compatible liquid or solid filler diluents or vehicles which are suitable for application to skin, hair, fur, and nails. The exact amount of carrier will depend upon the level of the UVA-absorbing dibenzoylmethane sunscreen active, the 2-ethylhexyl-p-methoxycinnamate and any other optional ingredients which one of ordinary skill in the art would classify as distinct from the carrier (e.g., other active components). The compositions of the present invention preferably comprise from about 20% to about 99.8%, more preferably from about 50% to about 99%, and most preferably from 75% to about 95%, by weight of the composition, of a carrier.

The carrier and compositions herein can be formulated in a number of ways, including but not limited to emulsions (in emulsion technology, a composition comprising a "dispersed phase" and a "continuous phase;" the dispersed phase existing as small particles or droplets that are suspended in and surrounded by a continuous phase). For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including creams, waxes, pastes, lotions, milks, mousses, gels, oils, tonics, and sprays. Preferred compositions are formulated into lotions, creams, gels, and sprays. These product forms may be used for a number of applications, including, but not limited to, hand and body lotions, cold creams, facial moisturizers, anti-acne preparations, topical analgesics, make-ups/cosmetics including foundations, eyeshadows, lipsticks, and the like as well as coatings (e.g., paints, varnishes, polishes, adhesives, etc.), household care items (e.g., detergents, cleansers, fabric conditioners, etc.), automotive and marine vehicle care items (e.g., waxes, etc.), hair care and styling products (e.g., shampoos, conditioners, gels, mousses, sprays, etc.), topical animal care items (e.g., shampoos, conditioners, skin treatments, etc.). Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons. A more complete disclosure of propellants useful herein can be found in Sagarin, *Cosmetics Science and Technology*, 2nd Edition, Vol. 2, pp. 443–465 (1972).

Optional Components

The compositions of the present invention may contain a variety of other ingredients such as are conventionally used in a given product type provided that they do not unacceptably alter the benefits of the invention.

In a preferred embodiment, where the composition is to be in contact with human skin, the optional components should be suitable for application to skin, that is, when incorporated into the composition they are suitable for use in contact with human skin without undue toxicity, incompatibility, instability, allergic response, and the like within the scope of sound medical judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

The compositions of the present invention may contain one or more of such optional components. Preferred compositions optionally contain one or more materials selected from UVB sunscreen actives, anti-acne actives, vitamin compounds, skin treating agents, humectants, moisturizers, skin conditioners, thickening agents, structuring agents, and emulsifiers.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

a) UVB Sunscreen Active

The compositions of the present invention may comprise one or more UVB sunscreen actives other than 2-ethylhexyl-p-methoxycinnamate, which absorb UV radiation having a wavelength of from about 290 nm to about 320 nm. As used herein the UVB sunscreen active means an active other than the UVA-absorbing dibenzoylmethane sunscreen active which itself may possess UVB absorption properties. The compositions comprise an amount of the UVB sunscreen active which is safe and effective to provide UVB protection either independently or in combination with other UV protective actives which may be present in the composition, preferably from about 0.1% to about 30%, more preferably from about 0.5% to about 25%, and most preferably from about 1% to about 20% by weight of the composition.

A wide variety of UVB sunscreen actives, including both organic sunscreen actives and inorganic physical sunblocks, are suitable for use herein. Nonlimiting examples of such sunscreen actives are described in U.S. Pat. No. 5,087,445 issued Feb. 11, 1992 to Haffey et al; and U.S. Pat. Nos. 5,073,371 and 5,073,372, both issued on Dec. 17, 1991 to Turner et al Nonlimiting examples of suitable physical sunblocks are described in *CTFA International Cosmetic Ingredient Dictionary*, Sixth Edition, 1995, pp. 1026–28 and 1103.

Preferred UVB sunscreen actives are selected from the group consisting of 2-phenyl-benzimidazole-5-sulfonic acid, TEA salicylate, octyl salicylate, octyl dimethyl PABA, zinc oxide, titanium dioxide, and mixtures thereof. More preferred UVB sunscreen actives are selected from the group consisting of 2-phenylbezimidazole-5-sulfonic acid, octyl salicylate, and mixtures thereof. Salt and acid-neutralized forms of the acidic sunscreens are also useful herein.

b) Anti-Acne Actives

The compositions of the present invention may comprise one or more anti-acne actives. Examples of useful anti-acne actives include resorcinol, sulfur, salicylic acid, erythromycin, zinc, etc. Further examples of suitable anti-acne actives are described in further detail in U.S. Pat. No. 5,607,980, issued to McAtee et al, on Mar. 4, 1997.

c) Vitamin Compounds

The compositions of the present invention may comprise vitamin compounds, precursors, and derivatives thereof. These vitamin compounds may be in either natural or synthetic form. Suitable vitamin compounds include, but are not limited to, Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, etc.), and Vitamin K (e.g., phytonadione, menadione, phthiocol, etc.) compounds.

In particular, the compositions of the present invention may comprise a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997) which is incorporated by reference herein in its entirety. The compositions of the present invention preferably comprise from about 0.01% to about 50%, more preferably from about 0.1% to about 10%, even more preferably from about 0.5% to about 10%, and still more preferably from about 1% to about 5%, most preferably from about 2% to about 5%, of the vitamin $B_3$ compound.

As used herein, "vitamin $B_3$ compound" means a compound having the formula:

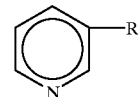

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Examples of suitable vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

The vitamin compounds may be included as the substantially pure material, or as an extract obtained by suitable physical and/or chemical isolation from natural (e.g., plant) sources.

d) Skin Treating Agent

The compositions of the present invention may contain one or more skin treating agents. Suitable skin treating agents include those effective for preventing, retarding, arresting, and/or reversing skin wrinkles. Examples of suitable skin treating agents include, but are not limited to, alpha-hydroxy acids such as lactic acid and glycolic acid and beta-hydroxy acids such as salicylic acid.

e) Structuring Agent

The compositions of the present invention may contain a structuring agent such as are known in the art. Structuring agents are particularly preferred in the oil-in-water emulsions of the present invention. Without being limited by theory, it is believed that the structuring agent assists in providing Theological characteristics to the composition which contribute to the stability of the composition. For example, the structuring agent tends to assist in the formation of the liquid crystalline gel network structures. The structuring agent may also function as an emulsifier or surfactant. Preferred compositions of this invention comprise from about 0.5% to about 20%, more preferably from about 1% to about 10%, most preferably from about 1% to about 5%, of one or more structuring agents.

The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of stearyl alcohol having an average of about 21 ethylene oxide units (steareth-21), the polyethylene glycol ether of cetyl alcohol having an average of about 2 ethylene oxide units, and mixtures thereof. Even more preferred structuring agents are selected from the group consisting of stearic acid, palmitic acid, stearyl alcohol, cetyl alcohol, behenyl alcohol, steareth-2, steareth-21, and mixtures thereof.

f) Thickening Agent (including thickeners and gelling agents

The compositions of the present invention can comprise one or more thickening agents, preferably from about 0.1% to about 5%, more preferably from about 0.1% to about 3%, and most preferably from about 0.25% to about 2%, by weight of the composition.

Nonlimiting classes of thickening agents include those selected from the group consisting of:

(i) Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. No. 5,087,445, to Haffey et al, issued Feb. 11, 1992; U.S. Pat. No. 4,509,949, to Huang et al, issued Apr. 5, 1985; U.S. Pat. No. 2,798,053, to Brown, issued Jul. 2, 1957; and in *CTFA International Cosmetic Ingredient Dictionary*, Fourth Edition, 1991, pp. 12 and 80.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from the group consisting of carbomers, acrylates/$C_{10}$–$C_{30}$ alkyl acrylate crosspolymers, and mixtures thereof.

(ii) Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987.

(iii) Polyacrylamide Polymers

The compositions of the present invention can optionally comprise polyacrylamide polymers, especially nonionic polyacrylamide polymers including substituted branched or unbranched polymers. Most preferred among these polyacrylamide polymers is the nonionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

(iv) Polysaccharides

A wide variety of polysaccharides are useful herein. "Polysaccharides" refer to gelling agents which contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$–$C_{30}$ straight chain or branched chain alkyl group through an ether linkage. Typically these polymers are ethers of $C_{10}$–$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1–3) linked glucose units with a (1–6) linked glucose every three units, a commercially available example of which is Clearogel™ CS11 from Michel Mercier Products Inc. (Mountainside, N.J.).

(v) Gums

Other thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Preferred compositions of the present invention include a thickening agent selected from the group consisting of carboxylic acid polymers, crosslinked polyacrylate polymers, polyacrylamide polymers, and mixtures thereof, more preferably selected from the group consisting of carboxylic acid polymers, polyacrylamide polymers, and mixtures thereof.

g) Humectants, Moisturizers, and Skin Conditioners

Preferred compositions optionally comprise one or more humectants, moisturizers, or skin conditioners. A variety of these materials can be employed and each can be present at a level of from about 0.01% to about 20%, more preferably from about 0.1% to about 10%, and most preferably from about 0.5% to about 7%. These materials include, but are not limited to, guanidine; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al, issued Dec. 11, 1990.

Also useful are various $C_1$–$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

g) Emulsifiers

The compositions of the present invention can comprise one or more emulsifiers, e.g., to reduce the interfacial tension between phases and improve the formulation and stability of an emulsion. Suitable emulsifiers include a wide variety of nonionic, cationic, anionic, and zwitterionic emulsifiers. See McCutcheon's, *Detergents and Emulsifiers*, North American Edition (1986), published by Allured Publishing Corporation; U.S. Pat. No. 5,011,681 issued to Ciotti et al on Apr. 30, 1991; U.S. Pat. No. 4,421,769 issued to Dixon et al on Dec. 20, 1983; and U.S. Pat. No. 3,755,560 issued to Dickert et al on Aug. 28, 1973.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers include, but are not limited to, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. Preferred emulsifiers are steareth-2, steareth-21, TEA stearate, diethanolamine cetyl phosphate, potassium cetyl phosphate, and mixtures thereof. The emulsifier can be used individually or as a mixture of two or more and comprises from about 0.1% to about 10%, more preferably from about 0.15% to about 7%, and most preferably from about 0.25% to about 5% of the compositions of the present invention.

While a variety of optional components may be included in the present compositions, the compositions are essentially free of benzylidene camphor derivatives. As used herein, "essentially free of benzylidene camphor derivatives" means the present compositions comprise less than about 0.1% of benzylidene camphor derivatives. Preferred compositions comprise less than about 0.05% of benzylidene camphor derivatives. Most preferably, the compositions are free of benzylidene camphor derivatives.

Furthermore, the compositions are essentially free of benzophenone derivatives. As used herein, "essentially free of benzophenone derivatives" means the present compositions comprise less than 0.5% of benzophenone derivatives. Preferred compositions comprise less than about 0.25% of benzophenone derivatives. Even more preferred composition comprise less than about 0.1% of benzophenone derivatives. It is most preferred, however, that the compositions of the present invention are free of benzophenone derivatives.

Methods For Providing Protection From UV Radiation

The compositions of the present invention are suitable for providing protection against the harmful effects of ultraviolet radiation, preferably in personal care products. More preferably, the compositions of the present invention are suitable for use as sunscreens to provide protection to human skin from the harmful effects of UV radiation which include, but are not limited to, sunburn and premature aging of the skin. The present invention therefore also further relates to methods of protecting human skin from the harmful effects of UV radiation. Such methods generally involve attenuating or reducing the amount of UV radiation which reaches the skin's surface. To protect the skin from UV radiation, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per $cm^2$ of skin to about 25 mg of composition per $cm^2$ of skin are typically applied.

Methods For Stabilizing Compositions Containing A UVA-Absorbing Dibenzoylmethane Sunscreen Active and 2-Ethylhexyl-p-methoxycinnamate The present invention also relates to a method of stabilizing a composition which comprises a UVA-absorbing dibenzoylmethane sunscreen active and 2-ethylhexyl-p-methoxycinnamate. The method comprises combining an effective amount of a UVA-absorbing dibenzoylmethane sunscreen active with a photostabilizing system which consists essentially of an effective amount of 2-ethylhexyl-p-methoxycinnamate such that the mole ratio of 2-ethylhexyl-p-methoxycinnamate to the dibenzoylmethane sunscreen active is from about 0.15:1 to about 1:1. Preferably, the method comprises the step of combining safe and effective amounts of the UVA-absorbing dibenzoylmethane sunscreen active and 2-ethylhexyl-p-methoxycinnamate such that the mole ratio of 2-ethylhexyl-p-methoxycinnamate to the dibenzoylmethane sunscreen active is from about 0.15:1 to about 1:1.

EXAMPLES

The following examples further describe and demonstrate embodiments within the scope of the present invention. The examples are given solely for the purpose of illustration and are not to be construed as limitations on the present invention, as many variations thereof are possible without departing from the spirit and scope of the invention.

The following sunscreen products are representative of the present invention.

| Component | Example I Wt % | Example II Wt % | Example III Wt % | Example IV Wt % | Example V Wt % |
|---|---|---|---|---|---|
| Water | QS100 | QS100 | QS100 | QS100 | QS100 |
| Glycerin | 3.00 | 3.00 | 6.00 | 2.00 | 6.00 |
| Disodium EDTA | 0.10 | 0.10 | 0.10 | 0.10 | 0.10 |
| Methyl Paraben | 0.25 | 0.25 | 0.25 | 0.25 | 0.25 |
| Sepigel 305 | 2.00 | 2.50 | 2.50 | 2.50 | 3.00 |
| Arlatone 2121 | — | 1.00 | — | — | — |
| 2-Phenyl-benzimidazole-5-sulphonic acid | — | 0.50 | — | 1.00 | 1.00 |
| Triethanolamine | — | 0.25 | — | 0.50 | 0.50 |
| Octyl Salicylate | 5.00 | 5.00 | — | 3.00 | 3.00 |
| Avobenzone | 2.00 | 2.00 | 3.00 | 2.00 | 1.00 |
| 2-Ethylhexy-p-methoxycinnamate | 1.50 | 1.30 | 2.00 | 1.33 | 0.90 |
| Isopropyl Palmitate | — | — | 4.00 | — | — |
| Caprylic/Capric Triglyceride | — | — | 4.00 | — | — |
| Isohexadecane | 2.00 | 3.00 | 2.00 | 2.00 | 3.00 |
| Steareth-21 | 0.80 | — | — | — | 0.80 |
| Steareth-2 | 0.10 | — | — | — | 0.10 |
| Cetyl Alcohol | 0.80 | 0.70 | 0.80 | 0.70 | 0.80 |
| Stearyl Alcohol | 0.80 | 0.50 | 0.80 | 0.70 | 0.80 |
| Behenyl Alcohol | 0.80 | — | 0.80 | — | 0.80 |
| Propyl Paraben | 0.15 | 0.15 | 0.15 | 0.15 | 0.15 |
| PEG-100 Stearate | — | 0.10 | — | 0.10 | — |

Prepare a water phase by combining the water, glycerin, disodium EDTA, methyl paraben and if present, Arlatone 2121 in an appropriate vessel with mixing and heating to approximately 75° C. Prepare the oil phase by combining the avobenzone, 2-ethylhexyl-p-methoxycinnamate, isohexadecane, cetyl alcohol, stearyl alcohol, propyl paraben and if present, octyl salicylate, isopropyl palmitate, caprylic/capric triglyceride, steareth-21, steareth-2, behenyl alcohol and PEG-100 stearate into a separate vessel with mixing and heating to approx. 75° C. Next, mix the oil phase into the water phase with shearing to form an emulsion. Cool the emulsion to 60° C. with shearing and add Sepigel 305 and if present, 2-phenyl-benzimidazole-5-sulphonic acid, and triethanolamine. Slowly stir the emulsion and cool to approximately 30° C. and package as desired.

What is claimed is:

1. A photostable composition suitable for providing protection against the harmful effects of ultraviolet radiation, said composition comprising:

a) a safe and effective amount of a UVA-absorbing dibenzoylmethane sunscreen active;

b) a photostabilizing system consisting essentially of a safe and effective amount of 2-ethylhexyl-p-methoxycinnamate; and c) a suitable carrier;

wherein the mole ratio of 2-ethylhexyl-p-methoxycinnamate to the dibenzoylmethane sunscreen active is from about 0.15:1 to about 1:1.

2. The composition of claim 1 wherein the UVA-absorbing dibenzoylmethane sunscreen active is selected from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4'tert-butyl-4'methoxydibenzoylmethane, and mixtures thereof.

3. The composition of claim 1 wherein the UVA-absorbing dibenzoylmethane sunscreen active is selected from the group consisting of 4-tert-butyl-4'-methoxydibenzoylmethane, isopropyldibenzoylmethane, and mixtures thereof.

4. The composition of claim 1 wherein the UVA-absorbing dibenzoylmethane sunscreen active is 4-tert-butyl-4'-methoxydibenzoylmethane.

5. The composition of claim 1 wherein the composition comprises from about 0.01% to about 30%, by weight of the composition, of the UVA-absorbing dibenzoylmethane sunscreen active.

6. The composition of claim 1 wherein the composition comprises from about 0.1% to about 6%, by weight of the composition, of the UVA-absorbing dibenzoylmethane sunscreen active.

7. The composition of claim 1 wherein the composition comprises from about 1% to about 3%, by weight of the composition, of the UVA-absorbing dibenzoylmethane sunscreen active.

8. The composition of claim 1 wherein the mole ratio of 2-ethylhexyl-p-methoxycinnamate to UVA-absorbing dibenzoylmethane sunscreen active is from about 0.3:1 to about 0.9:1.

9. The composition of claim 1 wherein the mole ratio of 2-ethylhexyl-p-methoxycinnamate to UVA-absorbing dibenzoylmethane sunscreen active is from about 0.45:1 to about 0.8:1.

10. The composition of claim 1 wherein the mole ratio of 2-ethylhexyl-p-methoxycinnamate to UVA-absorbing dibenzoylmethane sunscreen active is from about 0.6:1 to about 0.75:1.

11. The composition of claim 1 wherein the mole ratio of 2-ethylhexyl-p-methoxycinnamate to UVA-absorbing dibenzoylmethane sunscreen active is from about 0.65:1 to about 0.75:1.

12. The composition of claim 1 which further comprises a UVB sunscreen active selected from the group consisting of 2-phenyl-benzimidazole-5-sulfonic acid, TEA salicylate, octyl salicylate, octyl dimethyl PABA, zinc oxide, titanium dioxide, and mixtures thereof.

13. The composition of claim 1 wherein the UVB sunscreen active is selected from the group consisting of 2-phenyl-benzimidazole-5-sulfonic acid, octyl salicylate, and mixtures thereof.

14. The composition of claim 1 wherein the photostabilizing system consists of a safe and effective amount of 2-ethylhexyl-p-methoxycinnamate.

15. A photostable composition suitable for providing protection against the harmful effects of ultraviolet radiation, said composition comprising:
   a) a safe and effective amount of a UVA-absorbing dibenzoylmethane sunscreen active;
   b) a photostabilizing system comprising a safe and effective amount of 2-ethylhexyl-p-methoxycinnamate; and
   c) a suitable carrier;
   wherein the mole ratio of 2-ethylhexyl-p-methoxycinnamate to the dibenzoylmethane sunscreen active is from about 0.15:1 to about 1:1 and wherein said composition is essentially free of benzylidene camphor derivatives and benzophenone derivatives.

16. A method for providing protection against the harmful effects of ultraviolet radiation, said method comprising applying a safe and effective amount of the photostable composition of claim 1 to the skin.

17. A photostable composition suitable for providing protection against the harmful effects of ultraviolet radiation, said composition comprising:
   a) an effective amount of a UVA-absorbing dibenzoylmethane sunscreen active;
   b) a photostabilizing system consisting essentially of an effective amount of 2-ethylhexyl-p-methoxycinnamate; and
   c) a suitable carrier;
   wherein the mole ratio of 2-ethylhexyl-p-methoxycinnamate to the dibenzoylmethane sunscreen active is from about 0.15:1 to about 1:1.

18. An animal care product comprising the composition of claim 17.

19. An automotive care product comprising the composition of claim 17.

20. A household care product comprising the composition of claim 17.

21. A method of stabilizing a composition comprising a UVA-absorbing dibenzoylmethane sunscreen active and 2-ethylhexyl-p-methoxycinnamate, said method comprising the step of combining an effective amount of a UVA-absorbing dibenzoylmethane sunscreen active with a photostabilizing system which consists essentially of an effective amount of 2-ethylhexyl-p-methoxycinnamate wherein the mole ratio of 2-ethylhexyl-p-methoxycinnamate to the dibenzoylmethane sunscreen active is from about 0.15:1 to about 1:1.

* * * * *